United States Patent
Naumann et al.

[11] Patent Number: 5,962,638
[45] Date of Patent: Oct. 5, 1999

[54] PEPTIDES AND SYNTHETIC CELL MEMBRANES

[75] Inventors: Renate Naumann; Alfred Jonczyk, both of Darmstadt, Germany

[73] Assignee: Merck Patent Gesellschaft Mit Beschrankter Haftung, Germany

[21] Appl. No.: 08/849,825

[22] PCT Filed: Nov. 29, 1995

[86] PCT No.: PCT/EP95/04681

§ 371 Date: Jun. 13, 1997

§ 102(e) Date: Jun. 13, 1997

[87] PCT Pub. No.: WO96/18645

PCT Pub. Date: Jun. 20, 1996

[30] Foreign Application Priority Data

Dec. 16, 1994 [DE] Germany ............................ 44 44 893

[51] Int. Cl.⁶ .................................................. C07K 7/00
[52] U.S. Cl. ........................ 530/329; 530/328; 530/330; 436/524; 436/525
[58] Field of Search .................................. 530/328, 329, 530/330; 436/524, 525

[56] References Cited

PUBLICATIONS

Erdelen, C. et al. (1994), "Self–Assembled Disulfide–Functionalized Amphiphilic Copolymers on Gold," Langmuir, 10, 1246–1250.
Survay, M.. et al. (1993). "Oligoglycines and oligoalanines as tests for modelling mobility of peptides in capillary electrophoresis," Journal of Chromatography, 636, 81–86.
Head–Gordon, T. et al. (1991). "Virtual Rigid Body Dynamics," Biopolymers, 31, 77–100.
Schellenberger, V. (1993). "Mapping the S' Subsites of Serine Proteases Using Acyl Transfer to Mixtures of Peptide Nucleophiles†," Biochemistry, 32, 4349–4353.
Schleifer, K. et al. (1974). "The Immunochemistry of Peptidoglycan," Eur. J. Biochem, 43, 509–519.
Naumann, R. et al. (1995). "Incorporation of Membrane Proteins in Solid–Supported Lipid Layers," Agnew Chem. Int. Ed. Engl., 34, 2056–58.
Rothe, U. et al. (1989). "Lipid–Coated Particles—A New Approach to Fix Membrane–Bound Enzymes onto Carrier Surfaces," Biotechnology, 11, 18–30.
Lang, H. et al (1994). "A New Class of Thiolipids for the Attachment of Lipid Bilayers on Gold Surfaces," Langmuir, 10, 197–210.
Rothe, U. et al. (1990). "Oriented incorporation of bacteriorhodopsin into the lipid shell of phospholipid–coated polymer particles," FEBS Letters, 263, 308–312.
Lee et al., *Biochim. Biophys. Acta*, 1151 (1), 76–82, 1993.
Head–Gordon et al., *Biopolymers*, vol. 31, pp. 77–100, 1991.
Survay et al., *Journal of Chromat.*, 636, pp. 81–86, 1993.
Kojro et al., *Pol. J. Chem.*, 58(1–2–3), 163–71, 1984.

*Primary Examiner*—Cecilia J. Tsang
*Assistant Examiner*—C. Delacroix-Muirheid
*Attorney, Agent, or Firm*—Millen, White, Zelano, & Branigan, P.C.

[57] ABSTRACT

Linear peptides of the formula (I) R-A-B-C-D-E-OH, where R, A, B, C, D and E have the indicated meanings, are disclosed. Methods of making these peptides, and of using them as biosensors, solar cells and membrane models for use in the investigation of biochemical processes are disclosed.

16 Claims, No Drawings

SEQUENCE LISTING

<160> NUMBER OF SEQ ID NOS: 51

<210> SEQ ID NO 1
<211> LENGTH: 21
<212> TYPE: PRT
<213> ORGANISM: Artificial Sequence
<220> FEATURE:
<223> OTHER INFORMATION: Description of Artificial Sequence: PEPTIDE
<220> FEATURE:
<221> NAME/KEY: PEPTIDE
<222> LOCATION: (21)
<223> OTHER INFORMATION: leu-NH2"

<400> SEQUENCE: 1

Leu Ser Ser Leu Leu Ser Leu Leu Ser Ser Leu Leu Ser Leu Leu Ser
 1               5                  10                  15

Ser Leu Leu Ser Leu
            20

<210> SEQ ID NO 2
<211> LENGTH: 21
<212> TYPE: PRT
<213> ORGANISM: Artificial Sequence
<220> FEATURE:

```
<223> OTHER INFORMATION: Description of Artificial Sequence: PEPTIDE
<220> FEATURE:
<221> NAME/KEY: PEPTIDE
<222> LOCATION: (21)
<223> OTHER INFORMATION: leu-NH2"

<400> SEQUENCE: 2

Leu Ser Leu Leu Leu Ser Leu Leu Ser Leu Leu Leu Ser Leu Leu Ser
  1               5                   10                  15

Leu Leu Leu Ser Leu
            20

<210> SEQ ID NO 3
<211> LENGTH: 5
<212> TYPE: PRT
<213> ORGANISM: Artificial Sequence
<220> FEATURE:
<223> OTHER INFORMATION: Description of Artificial Sequence: PEPTIDE
<220> FEATURE:
<221> NAME/KEY: PEPTIDE
<222> LOCATION: (5)
<223> OTHER INFORMATION: Ala- OMet

<400> SEQUENCE: 3

Ala Ala Ala Ala Ala
  1               5

<210> SEQ ID NO 4
<211> LENGTH: 7
<212> TYPE: PRT
<213> ORGANISM: Artificial Sequence
<220> FEATURE:
<223> OTHER INFORMATION: Description of Artificial Sequence: PEPTIDE
<220> FEATURE:
<221> NAME/KEY: PEPTIDE
<222> LOCATION: (1)
<223> OTHER INFORMATION: Trt-S-(CH2)2-CO- Ala

<400> SEQUENCE: 4

Ala Ser Ser Ala Ala Ser Ala
  1               5

<210> SEQ ID NO 5
<211> LENGTH: 7
<212> TYPE: PRT
<213> ORGANISM: Artificial Sequence
<220> FEATURE:
<223> OTHER INFORMATION: Description of Artificial Sequence: PEPTIDE
<220> FEATURE:
<221> NAME/KEY: PEPTIDE
<222> LOCATION: (1)
<223> OTHER INFORMATION: HS-(CH2)2-CO - Ala

<400> SEQUENCE: 5

Ala Ser Ser Ala Ala Ser Ala
  1               5

<210> SEQ ID NO 6
<211> LENGTH: 5
<212> TYPE: PRT
<213> ORGANISM: Artificial Sequence
<220> FEATURE:
<223> OTHER INFORMATION: Description of Artificial Sequence: PEPTIDE
<220> FEATURE:
<221> NAME/KEY: PEPTIDE
<222> LOCATION: (1)
<223> OTHER INFORMATION: Trt-S-(CH2)2-CO- Ala

<400> SEQUENCE: 6

Ala Ala Ala Ala Ala
```

-continued

```
<210> SEQ ID NO 7
<211> LENGTH: 5
<212> TYPE: PRT
<213> ORGANISM: Artificial Sequence
<220> FEATURE:
<223> OTHER INFORMATION: Description of Artificial Sequence: PEPTIDE
<220> FEATURE:
<221> NAME/KEY: PEPTIDE
<222> LOCATION: (1)
<223> OTHER INFORMATION: HS-(CH2)2-CO- Ala

<400> SEQUENCE: 7

Ala Ala Ala Ala Ala
 1               5

<210> SEQ ID NO 8
<211> LENGTH: 5
<212> TYPE: PRT
<213> ORGANISM: Artificial Sequence
<220> FEATURE:
<223> OTHER INFORMATION: Description of Artificial Sequence: PEPTIDE
<220> FEATURE:
<221> NAME/KEY: PEPTIDE
<222> LOCATION: (1)
<223> OTHER INFORMATION: 5-(1,2-Dithiocyclopentan-3-yl)-pentanoyl- Ala

<400> SEQUENCE: 8

Ala Ala Ala Ala Ala
 1               5

<210> SEQ ID NO 9
<211> LENGTH: 9
<212> TYPE: PRT
<213> ORGANISM: Artificial Sequence
<220> FEATURE:
<223> OTHER INFORMATION: Description of Artificial Sequence: PEPTIDE
<220> FEATURE:
<221> NAME/KEY: PEPTIDE
<222> LOCATION: (1)
<223> OTHER INFORMATION: Trt-S-(CH2)2-CO-NH-(CH2)10-CO- Gly

<400> SEQUENCE: 9

Gly Gly Gly Arg Gly Asp Ser Pro Lys
 1               5

<210> SEQ ID NO 10
<211> LENGTH: 9
<212> TYPE: PRT
<213> ORGANISM: Artificial Sequence
<220> FEATURE:
<223> OTHER INFORMATION: Description of Artificial Sequence: PEPTIDE
<220> FEATURE:
<221> NAME/KEY: PEPTIDE
<222> LOCATION: (1)
<223> OTHER INFORMATION: HS-(CH2)2-CO-NH-(CH2)10-CO- Gly

<400> SEQUENCE: 10

Gly Gly Gly Arg Gly Asp Ser Pro Lys
 1               5

<210> SEQ ID NO 11
<211> LENGTH: 5
<212> TYPE: PRT
<213> ORGANISM: Artificial Sequence
<220> FEATURE:
<223> OTHER INFORMATION: Description of Artificial Sequence: PEPTIDE
<220> FEATURE:
<221> NAME/KEY: PEPTIDE
<222> LOCATION: (1)
```

```
<223> OTHER INFORMATION: Fmoc- Ala

<400> SEQUENCE: 11

Ala Ala Ala Ala Ala
 1               5

<210> SEQ ID NO 12
<211> LENGTH: 5
<212> TYPE: PRT
<213> ORGANISM: Artificial Sequence
<220> FEATURE:
<223> OTHER INFORMATION: Description of Artificial Sequence: PEPTIDE
<220> FEATURE:
<221> NAME/KEY: PEPTIDE
<222> LOCATION: (5)
<223> OTHER INFORMATION: Ala - Wang Resin

<400> SEQUENCE: 12

Ala Ala Ala Ala Ala
 1               5

<210> SEQ ID NO 13
<211> LENGTH: 7
<212> TYPE: PRT
<213> ORGANISM: Artificial Sequence
<220> FEATURE:
<223> OTHER INFORMATION: Description of Artificial Sequence: PEPTIDE
<220> FEATURE:
<221> NAME/KEY: PEPTIDE
<222> LOCATION: (1)
<223> OTHER INFORMATION: Fmoc- Ala
<220> FEATURE:
<221> NAME/KEY: PEPTIDE
<222> LOCATION: (2)
<223> OTHER INFORMATION: Ser(But)
<220> FEATURE:
<221> NAME/KEY: PEPTIDE
<222> LOCATION: (3)
<223> OTHER INFORMATION: Ser(But)
<220> FEATURE:
<221> NAME/KEY: PEPTIDE
<222> LOCATION: (6)
<223> OTHER INFORMATION: Ser(But)

<400> SEQUENCE: 13

Ala Ser Ser Ala Ala Ser Ala
 1               5

<210> SEQ ID NO 14
<211> LENGTH: 7
<212> TYPE: PRT
<213> ORGANISM: Artificial Sequence
<220> FEATURE:
<223> OTHER INFORMATION: Description of Artificial Sequence: PEPTIDE
<220> FEATURE:
<221> NAME/KEY: PEPTIDE
<222> LOCATION: (2)
<223> OTHER INFORMATION: Ser(But)
<220> FEATURE:
<221> NAME/KEY: PEPTIDE
<222> LOCATION: (3)
<223> OTHER INFORMATION: Ser(But)
<220> FEATURE:
<221> NAME/KEY: PEPTIDE
<222> LOCATION: (6)
<223> OTHER INFORMATION: Ser(But)

<400> SEQUENCE: 14

Ala Ser Ser Ala Ala Ser Ala
 1               5

<210> SEQ ID NO 15
```

```
<211> LENGTH: 9
<212> TYPE: PRT
<213> ORGANISM: Artificial Sequence
<220> FEATURE:
<223> OTHER INFORMATION: Description of Artificial Sequence: PEPTIDE
<220> FEATURE:
<221> NAME/KEY: PEPTIDE
<222> LOCATION: (4)
<223> OTHER INFORMATION: Arg(Mtr)
<220> FEATURE:
<221> NAME/KEY: PEPTIDE
<222> LOCATION: (6)
<223> OTHER INFORMATION: Asp(O-But)
<220> FEATURE:
<221> NAME/KEY: PEPTIDE
<222> LOCATION: (7)
<223> OTHER INFORMATION: Ser(But)
<220> FEATURE:
<221> NAME/KEY: PEPTIDE
<222> LOCATION: (9)
<223> OTHER INFORMATION: Lys(BOC)-Wang Resin
<220> FEATURE:
<221> NAME/KEY: PEPTIDE
<222> LOCATION: (1)
<223> OTHER INFORMATION: Fmoc - Gly

<400> SEQUENCE: 15

Gly Gly Gly Arg Gly Asp Ser Pro Lys
 1               5

<210> SEQ ID NO 16
<211> LENGTH: 9
<212> TYPE: PRT
<213> ORGANISM: Artificial Sequence
<220> FEATURE:
<223> OTHER INFORMATION: Description of Artificial Sequence: PEPTIDE
<220> FEATURE:
<221> NAME/KEY: PEPTIDE
<222> LOCATION: (4)
<223> OTHER INFORMATION: Arg(Mtr)
<220> FEATURE:
<221> NAME/KEY: PEPTIDE
<222> LOCATION: (6)
<223> OTHER INFORMATION: Asp(O-But)
<220> FEATURE:
<221> NAME/KEY: PEPTIDE
<222> LOCATION: (7)
<223> OTHER INFORMATION: Ser(But)
<220> FEATURE:
<221> NAME/KEY: PEPTIDE
<222> LOCATION: (9)
<223> OTHER INFORMATION: Lys(BOC)-Wang Resin

<400> SEQUENCE: 16

Gly Gly Gly Arg Gly Asp Ser Pro Lys
 1               5

<210> SEQ ID NO 17
<211> LENGTH: 9
<212> TYPE: PRT
<213> ORGANISM: Artificial Sequence
<220> FEATURE:
<223> OTHER INFORMATION: Description of Artificial Sequence: PEPTIDE
<220> FEATURE:
<221> NAME/KEY: PEPTIDE
<222> LOCATION: (4)
<223> OTHER INFORMATION: Arg(Mtr)
<220> FEATURE:
<221> NAME/KEY: PEPTIDE
<222> LOCATION: (6)
<223> OTHER INFORMATION: Asp(O-But)
<220> FEATURE:
<221> NAME/KEY: PEPTIDE
<222> LOCATION: (7)
<223> OTHER INFORMATION: Ser(But)
<220> FEATURE:
```

```
<221> NAME/KEY: PEPTIDE
<222> LOCATION: (9)
<223> OTHER INFORMATION: Lys(BOC)-Wang Resin
<220> FEATURE:
<221> NAME/KEY: PEPTIDE
<222> LOCATION: (1)
<223> OTHER INFORMATION: Trt-S-(CH2)2-CO-NH-(CH2)10-CO- Gly

<400> SEQUENCE: 17

Gly Gly Gly Arg Gly Asp Ser Pro Lys
  1               5

<210> SEQ ID NO 18
<211> LENGTH: 9
<212> TYPE: PRT
<213> ORGANISM: Artificial Sequence
<220> FEATURE:
<223> OTHER INFORMATION: Description of Artificial Sequence: PEPTIDE
<220> FEATURE:
<221> NAME/KEY: PEPTIDE
<222> LOCATION: (4)
<223> OTHER INFORMATION: Arg(Mtr)
<220> FEATURE:
<221> NAME/KEY: PEPTIDE
<222> LOCATION: (7)
<223> OTHER INFORMATION: Ser(But)
<220> FEATURE:
<221> NAME/KEY: PEPTIDE
<222> LOCATION: (9)
<223> OTHER INFORMATION: Lys(BOC)
<220> FEATURE:
<221> NAME/KEY: PEPTIDE
<222> LOCATION: (1)
<223> OTHER INFORMATION: Trt-S-(CH2)2-CO-NH-(CH2)10-CO - Gly
<220> FEATURE:
<221> NAME/KEY: PEPTIDE
<222> LOCATION: (6)
<223> OTHER INFORMATION: Asp(O-But)

<400> SEQUENCE: 18

Gly Gly Gly Arg Gly Asp Ser Pro Lys
  1               5

<210> SEQ ID NO 19
<211> LENGTH: 5
<212> TYPE: PRT
<213> ORGANISM: Artificial Sequence
<220> FEATURE:
<223> OTHER INFORMATION: Description of Artificial Sequence: PEPTIDE
<220> FEATURE:
<221> NAME/KEY: PEPTIDE
<222> LOCATION: (1)
<223> OTHER INFORMATION: Trt-S-(CH2)2-CO-NH-(CH2)10-CO- Ala

<400> SEQUENCE: 19

Ala Ala Ala Ala Ala
  1               5

<210> SEQ ID NO 20
<211> LENGTH: 7
<212> TYPE: PRT
<213> ORGANISM: Artificial Sequence
<220> FEATURE:
<223> OTHER INFORMATION: Description of Artificial Sequence: PEPTIDE
<220> FEATURE:
<221> NAME/KEY: PEPTIDE
<222> LOCATION: (2)
<223> OTHER INFORMATION: Ser(But)
<220> FEATURE:
<221> NAME/KEY: PEPTIDE
<222> LOCATION: (3)
<223> OTHER INFORMATION: Ser(But)
<220> FEATURE:
<221> NAME/KEY: PEPTIDE
```

-continued

```
<222> LOCATION: (6)
<223> OTHER INFORMATION: Ser(But)
<220> FEATURE:
<221> NAME/KEY: PEPTIDE
<222> LOCATION: (7)
<223> OTHER INFORMATION: Ala-Wang Resin

<400> SEQUENCE: 20

Ala Ser Ser Ala Ala Ser Ala
  1               5

<210> SEQ ID NO 21
<211> LENGTH: 7
<212> TYPE: PRT
<213> ORGANISM: Artificial Sequence
<220> FEATURE:
<223> OTHER INFORMATION: Description of Artificial Sequence: PEPTIDE
<220> FEATURE:
<221> NAME/KEY: PEPTIDE
<222> LOCATION: (1)
<223> OTHER INFORMATION: Trt-S-(CH2)2-CO-NH-(CH2)10-CO- Ala

<400> SEQUENCE: 21

Ala Ser Ser Ala Ala Ser Ala
  1               5

<210> SEQ ID NO 22
<211> LENGTH: 5
<212> TYPE: PRT
<213> ORGANISM: Artificial Sequence
<220> FEATURE:
<223> OTHER INFORMATION: Description of Artificial Sequence: PEPTIDE
<220> FEATURE:
<221> NAME/KEY: PEPTIDE
<222> LOCATION: (1)
<223> OTHER INFORMATION: HS-(CH2)2-CO-NH-(CH2)10-CO- Ala

<400> SEQUENCE: 22

Ala Ala Ala Ala Ala
  1               5

<210> SEQ ID NO 23
<211> LENGTH: 7
<212> TYPE: PRT
<213> ORGANISM: Artificial Sequence
<220> FEATURE:
<223> OTHER INFORMATION: Description of Artificial Sequence: PEPTIDE
<220> FEATURE:
<221> NAME/KEY: PEPTIDE
<222> LOCATION: (1)
<223> OTHER INFORMATION: HS-(CH2)2-CO-NH-(CH2)10-CO- Ala

<400> SEQUENCE: 23

Ala Ser Ser Ala Ala Ser Ala
  1               5

<210> SEQ ID NO 24
<211> LENGTH: 9
<212> TYPE: PRT
<213> ORGANISM: Artificial Sequence
<220> FEATURE:
<223> OTHER INFORMATION: Description of Artificial Sequence: PEPTIDE
<220> FEATURE:
<221> NAME/KEY: PEPTIDE
<222> LOCATION: (4)
<223> OTHER INFORMATION: Arg(Mtr)
<220> FEATURE:
<221> NAME/KEY: PEPTIDE
<222> LOCATION: (7)
<223> OTHER INFORMATION: Ser(But)
<220> FEATURE:
<221> NAME/KEY: PEPTIDE
```

```
<222> LOCATION: (9)
<223> OTHER INFORMATION: Lys(BOC)-Wang Resin
<220> FEATURE:
<221> NAME/KEY: PEPTIDE
<222> LOCATION: (1)
<223> OTHER INFORMATION: Trt-S-(CH2)2-CO- Gly
<220> FEATURE:
<221> NAME/KEY: PEPTIDE
<222> LOCATION: (6)
<223> OTHER INFORMATION: Asp(O-But)

<400> SEQUENCE: 24

Gly Gly Gly Arg Gly Asp Ser Pro Lys
 1               5

<210> SEQ ID NO 25
<211> LENGTH: 9
<212> TYPE: PRT
<213> ORGANISM: Artificial Sequence
<220> FEATURE:
<223> OTHER INFORMATION: Description of Artificial Sequence: PEPTIDE
<220> FEATURE:
<221> NAME/KEY: PEPTIDE
<222> LOCATION: (1)
<223> OTHER INFORMATION: Trt-S-(CH2)2-CO- Gly

<400> SEQUENCE: 25

Gly Gly Gly Arg Gly Asp Ser Pro Lys
 1               5

<210> SEQ ID NO 26
<211> LENGTH: 7
<212> TYPE: PRT
<213> ORGANISM: Artificial Sequence
<220> FEATURE:
<223> OTHER INFORMATION: Description of Artificial Sequence: PEPTIDE
<220> FEATURE:
<221> NAME/KEY: PEPTIDE
<222> LOCATION: (7)
<223> OTHER INFORMATION: Ala-Wang Resin

<400> SEQUENCE: 26

Ala Ser Ser Ala Ala Ser Ala
 1               5

<210> SEQ ID NO 27
<211> LENGTH: 9
<212> TYPE: PRT
<213> ORGANISM: Artificial Sequence
<220> FEATURE:
<223> OTHER INFORMATION: Description of Artificial Sequence: PEPTIDE
<220> FEATURE:
<221> NAME/KEY: PEPTIDE
<222> LOCATION: (4)
<223> OTHER INFORMATION: Arg(Mtr)
<220> FEATURE:
<221> NAME/KEY: PEPTIDE
<222> LOCATION: (7)
<223> OTHER INFORMATION: Ser(But)
<220> FEATURE:
<221> NAME/KEY: PEPTIDE
<222> LOCATION: (9)
<223> OTHER INFORMATION: Lys(BOC)-Wang Resin
<220> FEATURE:
<221> NAME/KEY: PEPTIDE
<222> LOCATION: (1)
<223> OTHER INFORMATION: 5-(1,2-Dithiocyclopentan-3-yl)-pentanoyl- Gly
<220> FEATURE:
<221> NAME/KEY: PEPTIDE
<222> LOCATION: (6)
<223> OTHER INFORMATION: Asp(O-But)

<400> SEQUENCE: 27
```

```
Gly Gly Gly Arg Gly Asp Ser Pro Lys
  1               5
```

<210> SEQ ID NO 28
<211> LENGTH: 9
<212> TYPE: PRT
<213> ORGANISM: Artificial Sequence
<220> FEATURE:
<223> OTHER INFORMATION: Description of Artificial Sequence: PEPTIDE
<220> FEATURE:
<221> NAME/KEY: PEPTIDE
<222> LOCATION: (1)
<223> OTHER INFORMATION: 5-(1,2-Dithiocyclopentan-3-yl)-pentanoyl- Gly

<400> SEQUENCE: 28

```
Gly Gly Gly Arg Gly Asp Ser Pro Lys
  1               5
```

<210> SEQ ID NO 29
<211> LENGTH: 7
<212> TYPE: PRT
<213> ORGANISM: Artificial Sequence
<220> FEATURE:
<223> OTHER INFORMATION: Description of Artificial Sequence: PEPTIDE
<220> FEATURE:
<221> NAME/KEY: PEPTIDE
<222> LOCATION: (1)
<223> OTHER INFORMATION: Trt-S-(CH2)2-CO-NH-(CH2)10-CO- Ala
<220> FEATURE:
<221> NAME/KEY: PEPTIDE
<222> LOCATION: (2)
<223> OTHER INFORMATION: Ser(But)
<220> FEATURE:
<221> NAME/KEY: PEPTIDE
<222> LOCATION: (3)
<223> OTHER INFORMATION: Ser(But)
<220> FEATURE:
<221> NAME/KEY: PEPTIDE
<222> LOCATION: (6)
<223> OTHER INFORMATION: Ser(But)

<400> SEQUENCE: 29

```
Ala Ser Ser Ala Ala Ser Ala
  1               5
```

<210> SEQ ID NO 30
<211> LENGTH: 9
<212> TYPE: PRT
<213> ORGANISM: Artificial Sequence
<220> FEATURE:
<223> OTHER INFORMATION: Description of Artificial Sequence: PEPTIDE
<220> FEATURE:
<221> NAME/KEY: PEPTIDE
<222> LOCATION: (4)
<223> OTHER INFORMATION: Arg(Mtr)
<220> FEATURE:
<221> NAME/KEY: PEPTIDE
<222> LOCATION: (7)
<223> OTHER INFORMATION: Ser(But)
<220> FEATURE:
<221> NAME/KEY: PEPTIDE
<222> LOCATION: (9)
<223> OTHER INFORMATION: Lys(BOC)
<220> FEATURE:
<221> NAME/KEY: PEPTIDE
<222> LOCATION: (1)
<223> OTHER INFORMATION: Trt-S-(CH2)2-CO - Gly
<220> FEATURE:
<221> NAME/KEY: PEPTIDE
<222> LOCATION: (6)
<223> OTHER INFORMATION: Asp(O-But)

<400> SEQUENCE: 30

Gly Gly Gly Arg Gly Asp Ser Pro Lys

-continued

```
<210> SEQ ID NO 31
<211> LENGTH: 7
<212> TYPE: PRT
<213> ORGANISM: Artificial Sequence
<220> FEATURE:
<223> OTHER INFORMATION: Description of Artificial Sequence: PEPTIDE
<220> FEATURE:
<221> NAME/KEY: PEPTIDE
<222> LOCATION: (1)
<223> OTHER INFORMATION: Trt-S-(CH2)2-CO- Ala
<220> FEATURE:
<221> NAME/KEY: PEPTIDE
<222> LOCATION: (2)
<223> OTHER INFORMATION: Ser(But)
<220> FEATURE:
<221> NAME/KEY: PEPTIDE
<222> LOCATION: (3)
<223> OTHER INFORMATION: Ser(But)
<220> FEATURE:
<221> NAME/KEY: PEPTIDE
<222> LOCATION: (6)
<223> OTHER INFORMATION: Ser(But)

<400> SEQUENCE: 31

Ala Ser Ser Ala Ala Ser Ala
 1               5

<210> SEQ ID NO 32
<211> LENGTH: 9
<212> TYPE: PRT
<213> ORGANISM: Artificial Sequence
<220> FEATURE:
<223> OTHER INFORMATION: Description of Artificial Sequence: PEPTIDE
<220> FEATURE:
<221> NAME/KEY: PEPTIDE
<222> LOCATION: (4)
<223> OTHER INFORMATION: Arg(Mtr)
<220> FEATURE:
<221> NAME/KEY: PEPTIDE
<222> LOCATION: (7)
<223> OTHER INFORMATION: Ser(But)
<220> FEATURE:
<221> NAME/KEY: PEPTIDE
<222> LOCATION: (9)
<223> OTHER INFORMATION: Lys(BOC)-Wang Resin
<220> FEATURE:
<221> NAME/KEY: PEPTIDE
<222> LOCATION: (1)
<223> OTHER INFORMATION: HS-(CH2)2-CO - Gly
<220> FEATURE:
<221> NAME/KEY: PEPTIDE
<222> LOCATION: (6)
<223> OTHER INFORMATION: Asp(O-But)

<400> SEQUENCE: 32

Gly Gly Gly Arg Gly Asp Ser Pro Lys
 1               5

<210> SEQ ID NO 33
<211> LENGTH: 9
<212> TYPE: PRT
<213> ORGANISM: Artificial Sequence
<220> FEATURE:
<223> OTHER INFORMATION: Description of Artificial Sequence: PEPTIDE
<220> FEATURE:
<221> NAME/KEY: PEPTIDE
<222> LOCATION: (4)
<223> OTHER INFORMATION: Arg(Mtr)
<220> FEATURE:
<221> NAME/KEY: PEPTIDE
<222> LOCATION: (7)
<223> OTHER INFORMATION: Ser(But)
<220> FEATURE:
```

```
<221> NAME/KEY: PEPTIDE
<222> LOCATION: (9)
<223> OTHER INFORMATION: Lys(BOC)
<220> FEATURE:
<221> NAME/KEY: PEPTIDE
<222> LOCATION: (1)
<223> OTHER INFORMATION: HS-(CH2)2-CO-NH-(CH2)10-CO - Gly
<220> FEATURE:
<221> NAME/KEY: PEPTIDE
<222> LOCATION: (6)
<223> OTHER INFORMATION: Asp(O-But)

<400> SEQUENCE: 33

Gly Gly Gly Arg Gly Asp Ser Pro Lys
  1               5

<210> SEQ ID NO 34
<211> LENGTH: 7
<212> TYPE: PRT
<213> ORGANISM: Artificial Sequence
<220> FEATURE:
<223> OTHER INFORMATION: Description of Artificial Sequence: PEPTIDE
<220> FEATURE:
<221> NAME/KEY: PEPTIDE
<222> LOCATION: (1)
<223> OTHER INFORMATION: HS-(CH2)2-CO-NH-(CH2)10-CO- Ala
<220> FEATURE:
<221> NAME/KEY: PEPTIDE
<222> LOCATION: (2)
<223> OTHER INFORMATION: Ser(But)
<220> FEATURE:
<221> NAME/KEY: PEPTIDE
<222> LOCATION: (3)
<223> OTHER INFORMATION: Ser(But)
<220> FEATURE:
<221> NAME/KEY: PEPTIDE
<222> LOCATION: (6)
<223> OTHER INFORMATION: Ser(But)

<400> SEQUENCE: 34

Ala Ser Ser Ala Ala Ser Ala
  1               5

<210> SEQ ID NO 35
<211> LENGTH: 7
<212> TYPE: PRT
<213> ORGANISM: Artificial Sequence
<220> FEATURE:
<223> OTHER INFORMATION: Description of Artificial Sequence: PEPTIDE
<220> FEATURE:
<221> NAME/KEY: PEPTIDE
<222> LOCATION: (1)
<223> OTHER INFORMATION: HS-(CH2)2-CO- Ala
<220> FEATURE:
<221> NAME/KEY: PEPTIDE
<222> LOCATION: (2)
<223> OTHER INFORMATION: Ser(But)
<220> FEATURE:
<221> NAME/KEY: PEPTIDE
<222> LOCATION: (3)
<223> OTHER INFORMATION: Ser(But)
<220> FEATURE:
<221> NAME/KEY: PEPTIDE
<222> LOCATION: (6)
<223> OTHER INFORMATION: Ser(But)

<400> SEQUENCE: 35

Ala Ser Ser Ala Ala Ser Ala
  1               5

<210> SEQ ID NO 36
<211> LENGTH: 9
<212> TYPE: PRT
<213> ORGANISM: Artificial Sequence
```

```
<220> FEATURE:
<223> OTHER INFORMATION: Description of Artificial Sequence: PEPTIDE
<220> FEATURE:
<221> NAME/KEY: PEPTIDE
<222> LOCATION: (4)
<223> OTHER INFORMATION: Arg(Mtr)
<220> FEATURE:
<221> NAME/KEY: PEPTIDE
<222> LOCATION: (7)
<223> OTHER INFORMATION: Ser(But)
<220> FEATURE:
<221> NAME/KEY: PEPTIDE
<222> LOCATION: (9)
<223> OTHER INFORMATION: Lys(BOC)
<220> FEATURE:
<221> NAME/KEY: PEPTIDE
<222> LOCATION: (1)
<223> OTHER INFORMATION: 5-(1,2-Dithiocyclopentan-3-yl)-pentanoyl- Gly
<220> FEATURE:
<221> NAME/KEY: PEPTIDE
<222> LOCATION: (6)
<223> OTHER INFORMATION: Asp(O-But)

<400> SEQUENCE: 36

Gly Gly Gly Arg Gly Asp Ser Pro Lys
 1               5

<210> SEQ ID NO 37
<211> LENGTH: 7
<212> TYPE: PRT
<213> ORGANISM: Artificial Sequence
<220> FEATURE:
<223> OTHER INFORMATION: Description of Artificial Sequence: PEPTIDE
<220> FEATURE:
<221> NAME/KEY: PEPTIDE
<222> LOCATION: (1)
<223> OTHER INFORMATION: 5-(1,2-Dithiocyclopentan-3-yl)-pentanoyl- Ala
<220> FEATURE:
<221> NAME/KEY: PEPTIDE
<222> LOCATION: (2)
<223> OTHER INFORMATION: Ser(But)
<220> FEATURE:
<221> NAME/KEY: PEPTIDE
<222> LOCATION: (3)
<223> OTHER INFORMATION: Ser(But)
<220> FEATURE:
<221> NAME/KEY: PEPTIDE
<222> LOCATION: (6)
<223> OTHER INFORMATION: Ser(But)

<400> SEQUENCE: 37

Ala Ser Ser Ala Ala Ser Ala
 1               5

<210> SEQ ID NO 38
<211> LENGTH: 7
<212> TYPE: PRT
<213> ORGANISM: Artificial Sequence
<220> FEATURE:
<223> OTHER INFORMATION: Description of Artificial Sequence: PEPTIDE
<220> FEATURE:
<221> NAME/KEY: PEPTIDE
<222> LOCATION: (1)
<223> OTHER INFORMATION: 5-(1,2-Dithiocyclopentan-3-yl)-pentanoyl- Ala

<400> SEQUENCE: 38

Ala Ser Ser Ala Ala Ser Ala
 1               5

<210> SEQ ID NO 39
<211> LENGTH: 7
<212> TYPE: PRT
<213> ORGANISM: Artificial Sequence
<220> FEATURE:
```

```
<223> OTHER INFORMATION: Description of Artificial Sequence: PEPTIDE
<220> FEATURE:
<221> NAME/KEY: PEPTIDE
<222> LOCATION: (1)
<223> OTHER INFORMATION: Aux [S-(CH2)2-CO- Ala]y

<400> SEQUENCE: 39

Ala Ser Ser Ala Ala Ser Ala
 1               5

<210> SEQ ID NO 40
<211> LENGTH: 5
<212> TYPE: PRT
<213> ORGANISM: Artificial Sequence
<220> FEATURE:
<223> OTHER INFORMATION: Description of Artificial Sequence: PEPTIDE
<220> FEATURE:
<221> NAME/KEY: PEPTIDE
<222> LOCATION: (1)
<223> OTHER INFORMATION: Aux-[S-(CH2)2-CO- Ala]y

<400> SEQUENCE: 40

Ala Ala Ala Ala Ala
 1               5

<210> SEQ ID NO 41
<211> LENGTH: 5
<212> TYPE: PRT
<213> ORGANISM: Artificial Sequence
<220> FEATURE:
<223> OTHER INFORMATION: Description of Artificial Sequence: PEPTIDE
<220> FEATURE:
<221> NAME/KEY: PEPTIDE
<222> LOCATION: (1)
<223> OTHER INFORMATION: Aux-[5-(1,2-Dithiocyclopentan-3yl)-pentanoyl-
      Ala]y"

<400> SEQUENCE: 41

Ala Ala Ala Ala Ala
 1               5

<210> SEQ ID NO 42
<211> LENGTH: 9
<212> TYPE: PRT
<213> ORGANISM: Artificial Sequence
<220> FEATURE:
<223> OTHER INFORMATION: Description of Artificial Sequence: PEPTIDE
<220> FEATURE:
<221> NAME/KEY: PEPTIDE
<222> LOCATION: (1)
<223> OTHER INFORMATION: Aux [S-(CH2)2-CO-NH-(CH2)10-CO- Gly]y

<400> SEQUENCE: 42

Gly Gly Gly Arg Gly Asp Ser Pro Lys
 1               5

<210> SEQ ID NO 43
<211> LENGTH: 9
<212> TYPE: PRT
<213> ORGANISM: Artificial Sequence
<220> FEATURE:
<221> NAME/KEY: PEPTIDE
<222> LOCATION: (1)
<223> OTHER INFORMATION: HS-(CH2)2-CO-NH-(CH2)10-CO - Gly
<220> FEATURE:
<221> NAME/KEY: PEPTIDE
<222> LOCATION: (4)
<223> OTHER INFORMATION: Arg(Mtr)
<220> FEATURE:
<221> NAME/KEY: PEPTIDE
<222> LOCATION: (6)
<223> OTHER INFORMATION: Asp(O-But)
```

```
<220> FEATURE:
<221> NAME/KEY: PEPTIDE
<222> LOCATION: (7)
<223> OTHER INFORMATION: Ser(But)
<220> FEATURE:
<221> NAME/KEY: PEPTIDE
<222> LOCATION: (9)
<223> OTHER INFORMATION: Lys(BOC)-Wang Resin
<220> FEATURE:
<223> OTHER INFORMATION: Description of Artificial Sequence: PEPTIDE

<400> SEQUENCE: 43

Gly Gly Gly Arg Gly Asp Ser Pro Lys
 1               5

<210> SEQ ID NO 44
<211> LENGTH: 9
<212> TYPE: PRT
<213> ORGANISM: Artificial Sequence
<220> FEATURE:
<221> NAME/KEY: PEPTIDE
<222> LOCATION: (1)
<223> OTHER INFORMATION: HS-(CH2)2-CO-NH-(CH2)10-CO - Gly
<220> FEATURE:
<223> OTHER INFORMATION: Description of Artificial Sequence: PEPTIDE

<400> SEQUENCE: 44

Gly Gly Gly Arg Gly Asp Ser Pro Lys
 1               5

<210> SEQ ID NO 45
<211> LENGTH: 9
<212> TYPE: PRT
<213> ORGANISM: Artificial Sequence
<220> FEATURE:
<221> NAME/KEY: PEPTIDE
<222> LOCATION: (1)
<223> OTHER INFORMATION: Lipoyl- Gly
<220> FEATURE:
<221> NAME/KEY: PEPTIDE
<222> LOCATION: (4)
<223> OTHER INFORMATION: Arg(Mtr)
<220> FEATURE:
<221> NAME/KEY: PEPTIDE
<222> LOCATION: (6)
<223> OTHER INFORMATION: Asp(O-But)
<220> FEATURE:
<221> NAME/KEY: PEPTIDE
<222> LOCATION: (7)
<223> OTHER INFORMATION: Ser(But)
<220> FEATURE:
<221> NAME/KEY: PEPTIDE
<222> LOCATION: (9)
<223> OTHER INFORMATION: Lys(BOC)-Wang Resin
<220> FEATURE:
<223> OTHER INFORMATION: Description of Artificial Sequence: PEPTIDE

<400> SEQUENCE: 45

Gly Gly Gly Arg Gly Asp Ser Pro Lys
 1               5

<210> SEQ ID NO 46
<211> LENGTH: 9
<212> TYPE: PRT
<213> ORGANISM: Artificial Sequence
<220> FEATURE:
<221> NAME/KEY: PEPTIDE
<222> LOCATION: (1)
<223> OTHER INFORMATION: Lipoyl - Gly
<220> FEATURE:
<223> OTHER INFORMATION: Description of Artificial Sequence: PEPTIDE

<400> SEQUENCE: 46
```

```
Gly Gly Gly Arg Gly Asp Ser Pro Lys
  1               5
```

<210> SEQ ID NO 47
<211> LENGTH: 5
<212> TYPE: PRT
<213> ORGANISM: Artificial Sequence
<220> FEATURE:
<221> NAME/KEY: PEPTIDE
<222> LOCATION: (1)
<223> OTHER INFORMATION: Lipoyl - Ala
<220> FEATURE:
<223> OTHER INFORMATION: Description of Artificial Sequence: PEPTIDE

<400> SEQUENCE: 47

```
Ala Ala Ala Ala Ala
  1           5
```

<210> SEQ ID NO 48
<211> LENGTH: 7
<212> TYPE: PRT
<213> ORGANISM: Artificial Sequence
<220> FEATURE:
<221> NAME/KEY: PEPTIDE
<222> LOCATION: (1)
<223> OTHER INFORMATION: Lipoyl - Ala
<220> FEATURE:
<223> OTHER INFORMATION: Description of Artificial Sequence: PEPTIDE

<400> SEQUENCE: 48

```
Ala Ser Ser Ala Ala Ser Ala
  1               5
```

<210> SEQ ID NO 49
<211> LENGTH: 9
<212> TYPE: PRT
<213> ORGANISM: Artificial Sequence
<220> FEATURE:
<221> NAME/KEY: PEPTIDE
<222> LOCATION: (1)
<223> OTHER INFORMATION: HS-(CH2)2-CO - Gly
<220> FEATURE:
<223> OTHER INFORMATION: Description of Artificial Sequence: PEPTIDE

<400> SEQUENCE: 49

```
Gly Gly Gly Arg Gly Asp Ser Pro Lys
  1               5
```

<210> SEQ ID NO 50
<211> LENGTH: 9
<212> TYPE: PRT
<213> ORGANISM: Artificial Sequence
<220> FEATURE:
<221> NAME/KEY: PEPTIDE
<222> LOCATION: (1)
<223> OTHER INFORMATION: HS-(CH2)2-CO - Gly
<220> FEATURE:
<221> NAME/KEY: PEPTIDE
<222> LOCATION: (4)
<223> OTHER INFORMATION: Arg(Mtr)
<220> FEATURE:
<221> NAME/KEY: PEPTIDE
<222> LOCATION: (6)
<223> OTHER INFORMATION: Asp(O-But)
<220> FEATURE:
<221> NAME/KEY: PEPTIDE
<222> LOCATION: (7)
<223> OTHER INFORMATION: Ser(But)
<220> FEATURE:
<221> NAME/KEY: PEPTIDE
<222> LOCATION: (9)
<223> OTHER INFORMATION: Lys(BOC)
<220> FEATURE:

-continued

```
<223> OTHER INFORMATION: Description of Artificial Sequence: PEPTIDE

<400> SEQUENCE: 50

Gly Gly Gly Arg Gly Asp Ser Pro Lys
 1               5

<210> SEQ ID NO 51
<211> LENGTH: 7
<212> TYPE: PRT
<213> ORGANISM: Artificial Sequence
<220> FEATURE:
<221> NAME/KEY: PEPTIDE
<222> LOCATION: (1)
<223> OTHER INFORMATION: Lipoyl - Ala
<220> FEATURE:
<221> NAME/KEY: PEPTIDE
<222> LOCATION: (2)
<223> OTHER INFORMATION: Ser(But)
<220> FEATURE:
<221> NAME/KEY: PEPTIDE
<222> LOCATION: (3)
<223> OTHER INFORMATION: Ser(But)
<220> FEATURE:
<221> NAME/KEY: PEPTIDE
<222> LOCATION: (6)
<223> OTHER INFORMATION: Ser(But)
<220> FEATURE:
<223> OTHER INFORMATION: Description of Artificial Sequence: PEPTIDE

<400> SEQUENCE: 51

Ala Ser Ser Ala Ala Ser Ala
 1               5
```

PEPTIDES AND SYNTHETIC CELL MEMBRANES

The invention relates to peptides or peptide-analogous compounds of the formula I

R-A-B-C-D-E-OH    I, in which
- A is an amino acid residue selected from a group consisting of Ala, Gly or Leu,
- B is an amino acid or dipeptide residue selected from a group consisting of Ala, Ser, Gly-Gly and Ser-Ser,
- C is an amino acid, di or tripeptide residue selected from a group consisting of Ala, Ala-Ala, Leu-Leu, Ala-Ala-Ala, Arg-Gly-Asp and Leu-Leu-Leu,
- D is an amino acid residue selected from a group consisting of Ala and Ser,
- E is an amino acid or dipeptide residue selected from a group consisting of Ala, Leu and Pro-Lys,
- R is H, HS-alkyl-CO, HS-alkyl-CO-NH-alkyl'-CO-, Trt-S-alkyl-CO-, Trt-S-alkyl-CO-NH-alkyl'-CO- or 1,2-dithiocyclopentane-3-$(CH_2)_4$—CO—, where R can be H only if at least one of the residues A, B, C, D or E is not Ala,
- alkyl and alkyl' are each, independently of one another, an alkylene radical with 1 to 11 C atoms and
Trt is triphenylmethyl,
and the salts thereof.

Lipids and proteins are major components of biological membranes. Lipid bilayers are regarded as a model of cell membranes. Peptides or proteins can be incorporated into such lipid bilayers so that they extend through them by insertion perpendicular to the surface (J. C. Huschilt et al. BBA 979, 139–141 (1989)). The conformation of such a bilayer is partly determined by the sequence of the peptide. J. D. Leer et al. (Science 240, 1177–1181 (1988)) were able to show that the peptide H-(Leu-Ser-Ser-Leu-Leu-Ser-Leu)$_3$—CONH$_2$ (SEQ ID NO:1) with a length which extends through the membrane forms, as amphiphilic alpha helix, an ion channel which arises due to self-organization of these helices in bundles. A peptide consisting of 14 amino acids with this sequence, which is too short to extend through the lipid bilayer, was unable to form this discrete channel. On the other hand, the peptide H-(Leu-Ser-Leu-Leu-Leu-Ser-Leu)$_3$—CONH$_2$ (SEQ ID NO:2) forms a proton channel.

Omega-substituted alkanethiols bind and organize themselves on gold surfaces (C. D. Bain et al., Angew. Chemie 101, 522–528 (1989)).

Alkanethiols (octanethiol and hexadecanethiol) form, on gold-coated electrodes, an organized monolayer on which lipid bilayers can be formed with lipids. Adsorption of proteins (cholera toxin) to the monolayer can be analyzed electrochemically (impedance measurement) and optically (surface plasmon resonance). The electrochemical measurement provides information on the quality of the layer and on the amount of ligand molecule inserted. The optical method permits the amount of lipid bound to gold, and the selective binding of the acceptor molecule (cholera toxin) to the membrane, to be quantified (S. Terrettaz et al. Langmuir 9, 1361–1369 (1993)).

The interaction of surface-bound anti-mouse IgG antibodies with mouse IgG as ligand has been measured not on gold but on tantalum/tantalum oxide. The change in impedance with this immunochemical reaction was analyzed in real time in a flow cell. The protein was not anchored via a thiol but bound via an aminoalkylsilane (A. Gebbert et al. Anal. Chem. 64, 997–1003 (1992)).

It was possible to load spherical particles of polymethylmethacrylate with H-(Ala)$_5$-OMe (SEQ ID NO:3) with the aid of a carbodiimide. After hydrolysis of the esters, it was possible to couple the lipid phosphatidylethanolamine to the carboxyl groups of the peptides. It was possible by adsorption of further phospholipids to form lipid bilayers into which bacteriorhodopsin was incorporated. It was possible to show, by detecting the direction of the proton pumps produced and electron microscopy that the preferred orientation of the bacteriorhodopsin in the lipid layer runs from the inside to the outside (U. Rothe et al. FEBS Lett. 263, 308–312 (1990)).

The invention was based on the object of finding novel compounds with valuable properties, in particular those which can be used to prepare peptide layers, peptide-analogous layers or cell membranes.

It has been found that mercaptoalkylcarboxy-peptides of the formula I are bound to gold surfaces and that they organize themselves to dense layers, especially when lipids (for example dimyristoylphosphatidyloxyethylamine, DMPE) are covalently coupled to the peptidylgold phase.

This produces on the gold surface monomolecular lipid layers which are covalently bonded via the peptide spacer group to the gold. Alternatively, lipid layers can also be applied to the peptide layer by the Langmuir-Boldgett technique. The method is described, for example, by G. Puu, I. Gustavson, P.-A. Ohlsson, G. Olofson and A. Sellstrøm in Progress in Membrane Biotechnologie page 279 et seq. (1991), Birkhäuser Verlag, Basel (Eds. Fernandez/Chapman/Packer).

The peptide spacer serves to form a hydrophilic layer between the hydrophobic lipid layer and the gold electrode. The lipid monolayer formed in this way can be provided with a second lipid layer, for example with the aid of the Langmuir-Boldgett technique or by rolling out liposomes, to result in defined lipid bilayers which represent a model of a biological membrane to the extent that they are adjacent to an aqueous phase on both sides. They are able to insert functional membrane proteins and thus permit their electrical, structural and binding properties to be investigated.

These lipid-peptide-gold constructs are accordingly capable of forming bilayers and inserting proteins. The formation and the order state of the layers can be measured by cyclovoltametry, impedance spectrometry and surface plasmon resonance spectroscopy (SPRS).

The compounds of the formula I can be employed as building blocks for synthetic peptide layers or biological membranes, in particular cell membranes.

The abbreviations of amino acid residues mentioned hereinbefore and hereinafter represent the residues of the following amino acids:

| | |
|---|---|
| Ala | alanine |
| Arg | arginine |
| Asp | aspartic acid |
| Cys | cysteine |
| Gly | glycine |
| Leu | leucine |
| Lys | lysine |
| Pro | proline |
| Ser | serine. |

Further meanings hereinafter are:

| | |
|---|---|
| BOC | tert-butoxycarbonyl |
| CBZ | benzyloxycarbonyl |
| DCCI | dicyclohexylcarbodiimide |
| DIC | diisopropylcarbodiimide |
| DMF | dimethylformamide |
| DMPE | dimyristoylphosphatidylethanolamine |
| EDC1 | N-ethyl-N'-(3-dimethylaminopropyl)carbodiimide hydrochloride |
| Et | ethyl |
| Fmoc | 9-fluorenylmethoxycarbonyl |
| HOBt | 1-hydroxybenzotriazole |
| Me | methyl |
| MBHA | 4-methylbenzhydrylamine |
| Mtr | 4-methoxy-2,3,6-trimethylphenylsulfonyl |
| OBut | tert-butyl ester |
| OMe | methyl ester |
| OEt | ethyl ester |
| POA | phenoxyacetyl |
| TFA | trifluoroacetic acid |
| Trt | trityl (triphenylmethyl). |

Where the abovementioned amino acids or residues thereof are able to occur in several enantiomeric forms, all these forms and also their mixtures (for example the DL forms) are included hereinbefore and hereinafter, for example as constituent of compounds of the formula I. It is furthermore possible for the amino acids or the amino acid residues to be derivatized in a form known per se.

The invention furthermore relates to a process for preparing a compound of the formula I according to Claim 1 or one of its salts, characterized in that it is liberated from one of its functional derivatives by treatment with a solvolyzing or hydrogenolyzing agent,
or in that a peptide of the formula II $$M\text{-}OH \quad \quad II$$

in which
M is R but not hydrogen, R-A, R-A-B, R-A-Gly, R-A-B-C, R-A-B-Leu, R-A-B-Arg, R-A-B-Arg-Gly or R-A-B-C-D
is reacted with an amino compound of the formula III $$H\text{-}Q\text{-}OH \quad \quad III$$

in which
Q is E, Lys, D-E, C-D-E, Leu-D-E, Asp-D-E, Gly-Asp-D-E, B-C-D-E, Gly-C-D-E, A-B-C-D-E or NH-alkyl'-CO-A-B-C-D-E,
and/or in that where appropriate a free amino group is acylated and/or a compound of the formula I is converted by treatment with an acid of a base into one of its salts.

The radicals A, B, C, D, E and R hereinbefore and hereinafter have the meanings stated for formulae I, II and III unless expressly stated otherwise.

In the above formulae, alkyl and alkyl' are, independently of one another, preferably $-CH_2-$, $-(CH_2)_2-$, $-(CH_2)_3-$, $-(CH_2)_4-$, $-(CH_2)_5-$, $-(CH_2)_9-$, $-(CH_2)_{10}-$ or $-(CH_2)_{11}-$.

R is preferably Trt-S-alkyl-CO, HS-alkyl-CO-, Trt-S-alkyl-CO-NH-alkyl'-CO-, HS-alkyl-CO-NH-alkyl'-CO- or 5-(1,2-dithio-3-cyclopentanyl)pentanoyl-.

Group A is preferably Ala or Gly. B is preferably Ser or Ser-Ser, but also Ala or Gly-Gly. C is preferably Ala, Ala-Ala or Arg-Gly-Asp. E is preferably Ala or Pro-Lys.

Accordingly, the invention particularly relates to those compounds of the formula I in which at least one of the radicals mentioned has one of the preferred meanings stated above.

A preferred group of compounds can be expressed by formula Ia which corresponds to formula I and in which B, C, E, X and Z have the meanings stated there, and
A is Ala,
B is Ala or Ser-Ser,
E is Ala or Pro-Lys.

Another group of preferred compounds can be expressed by the part-formulae Iaa to Iad which otherwise correspond to formulae I and Ia but in which, additionally,
in Iaa: R is HS-alkyl-CO-
in Iab: R is Trt-S-alkyl-CO-
in Iac: R is Trt-S-alkyl-CO-NH-alkyl'-CO-
in Iad: R is HS-alkyl-CO-NH-alkyl'-CO-.

Particularly suitable compounds of the formula I are:
(a) Trt-S—$(CH_2)_2$—CO-Ala-Ser-Ser-Ala-Ala-Ser-Ala-OH (SEQ ID NO:4);
(b) HS—$(CH_2)_2$—CO-Ala-Ser-Ser-Ala-Ala-Ser-Ala-OH (SEQ ID NO:5);
(c) Trt-S—$(CH_2)_2$—CO-Ala-Ala-Ala-Ala-Ala-OH (SEQ ID NO:6);
(d) HS—$(CH_2)_2$—CO-Ala-Ala-Ala-Ala-Ala-OH (SEQ ID NO:7);
(e) 5-(1,2-dithio-3-cyclopentanyl)pentanoyl-Ala-Ala-Ala-Ala-Ala-OH (SEQ ID NO:8);
(f) Trt-S—$(CH_2)_2$—CO—N—$(CH_2)_{10}$—CO-Gly-Gly-Gly-Arg-Gly-Asp-Ser-Pro-Lys-OH (SEQ ID NO:9);
(g) HS—$(CH_2)_2$—CO—N—$(CH_2)_{10}$—CO-Gly-Gly-Gly-Arg-Gly-Asp-Ser-Pro-Lys-OH (SEQ ID NO:10);
and the salts thereof.

The compounds of the formula I, and also the starting materials for preparing them, are otherwise prepared by known methods as described in the literature (for example in the standard works such as Houben-Weyl, Methoden der organischen Chemie [Methods of organic chemistry], Georg-Thieme-Verlag, Stuttgart), specifically under reaction conditions which are known and suitable for the reactions mentioned. It is moreover possible to make use of known variants which are not mentioned in detail here.

The starting materials can, if required, also be formed in situ, so that they are not isolated from the reaction mixture but immediately reacted further to give the compounds of the formula I.

The compounds of the formula I can be obtained by liberating them from their functional derivatives by solvolysis, in particular hydrolysis, or by hydrogenolysis.

Preferred starting materials for the solvolysis or hydrogenolysis are those which, in place of one or more free amino and/or hydroxyl groups, comprise corresponding protected amino and/or hydroxyl groups, preferably those which, in place of an H atom linked to an N atom, have an amino protective group, for example those which correspond to formula I but, in place of an $NH_2$ group, comprise an NHR' group (in which R' is an amino protective group, for example BOC or CBZ).

Further preferred starting materials are those which, in place of the H atom of a hydroxyl group, have a hydroxyl protective group, for example those which correspond to the formula I but, in place of a hydroxyphenyl group, comprise an R"O-phenyl group (in which R" is a hydroxyl protective group).

It is also possible for a plurality of identical or different protected amino and/or hydroxyl groups to be present in the molecule of the starting material. If the protective groups which are present differ from one another, they can in many cases be eliminated selectively.

The term "amino protective group" is generally known and refers to groups which are suitable for protecting (blocking) an amino group from chemical reactions but which can easily be removed after the required chemical reaction has been carried out elsewhere in the molecule. Typical of such groups are, in particular, unsubstituted or substituted acyl, aryl, aralkoxymethyl or aralkyl groups. Since the amino protective groups are removed after the required reaction (or sequence of reactions), their nature and size is not otherwise critical; however, those with 1–20, in particular 1–8, C atoms are preferred. The term "acyl group" is to be interpreted in the widest sense in connection with the present process and the present compounds. It embraces acyl groups derived from aliphatic, araliphatic, aromatic or heterocyclic carboxylic acids or sulfonic acids, and, in particular alkoxycarbonyl, aryloxycarbonyl and, especially, aralkoxycarbonyl groups. Examples of such acyl groups are alkanoyl such as acetyl, propionyl, butyryl; aralkanoyl such as phenylacetyl; aroyl such as benzoyl or toluyl; aryloxyalkanoyl such as POA; alkoxycarbonyl such as methoxycarbonyl, ethoxycarbonyl, 2,2,2-trichloroethoxycarbonyl, BOC, 2-iodoethoxycarbonyl; aralkyloxycarbonyl such as CBZ ("carbobenzoxy"), 4-methoxybenzyloxycarbonyl, Fmoc; arylsulfonyl such as Mtr. Preferred amino protective groups are BOC and Mtr.

The term "hydroxyl protective group" is likewise generally known and refers to groups which are suitable for protecting a hydroxyl group from chemical reactions but can easily be removed after the required chemical reaction has been carried out elsewhere in the molecule. Typical of such groups are the abovementioned unsubstituted or substituted aryl, aralkyl or acyl groups, as well as alkyl groups. The nature and size of the hydroxyl protective groups is not critical because they are removed again after the required chemical reaction or sequence of reactions; preferred groups have 1–20, in particular 1–10, C atoms. Examples of hydroxyl protective groups are, inter alia, benzyl, p-nitrobenzoyl, p-toluenesulfonyl and acetyl, with benzyl and acetyl being particularly preferred. The COOH groups in aspartic acid and glutamic acid are preferably protected in the form of their tert-butyl esters (for example Asp(OBut)).

The functional derivatives, which are to be used as starting materials, of the compounds of the formula I can be prepared by customary methods of amino acid and peptide synthesis as described, for example, in the standard works mentioned and patent applications, for example also by the Merrifield solid-phase method (B. F. Gysin & R. B. Merrifield, J. Am. Chem. Soc. 94, 3102 ff. (1972)).

The liberation of the compounds of the formula I from their functional derivatives takes place, depending on the protective group used, for example with strong acids, preferably with TFA or perchloric acid, or else with other strong inorganic acids such as hydrochloric acid or sulfuric acid, strong organic carboxylic acids such as trichloroacetic acid or sulfonic acids such as benzene- or p-toluenesulfonic acid. The presence of an additional inert solvent is possible but not always necessary. Suitable and preferred inert solvents are organic ones, for example carboxylic acids such a acetic acid, ethers such as tetrahydrofuran or dioxane, amides such as DMF, halogenated hydrocarbons such as dichloromethane, as well as alcohols such as methanol, ethanol or isopropanol, and water. Mixtures of the abovementioned solvents are also suitable. TFA is preferably used in excess without adding a further solvent, perchloric acid in the form of a mixture of acetic acid and 70% perchloric acid in the ratio 9:1. The reaction temperatures for the cleavage are preferably between about 0 and about 50°, preferably between 15 and 30° (room temperature).

The groups BOC, OBut and Mtr can, for example, be preferably eliminated with TFA in dichloromethane or with about 3 to 5 N HCl in dioxane at 15–30°, the Fmoc group with an approximately 5 to 50% solution of dimethylamine, diethylamine or piperidine in DMF at 15–30°.

Protective groups which can be removed by hydrogenolysis (for example CBZ or benzyl) can, for example, be eliminated by treatment with hydrogen in the presence of a catalyst (for example a noble metal catalyst such as palladium, preferably on a support such as carbon). Solvents suitable in this case are those indicated above, especially, for example, alcohols such as methanol or ethanol or amides such as DMF. The hydrogenolysis is, as a rule, carried out at temperatures between about 0 and 100° and under pressures between about 1 and 200 bar, preferably at 20–30° under 1–10 bar. Hydrogenolysis of the CBZ group takes place satisfactorily, for example, on 5 to 10% Pd-C in methanol or with ammonium formate (in place of $H_2$) on Pd-C in methanol/DMF at 20–30°.

Compounds of the formula I can also be obtained by reacting a compound of the formula II with an amino compound of the formula III under condensing conditions known per se for peptide syntheses, as described, for example, in Houben-Weyl, loc. cit., Volume 1-5/II, pages 1–806 (1974).

The reaction is preferably carried out in the presence of a dehydrating agent, for example of a carbodiimide such as DCCI or EDCI, furthermore propanephosphonic anhydride (compare Angew. Chem. 92, 129 (1980)), diphenylphosphoryl azide or 2-ethoxy-N-ethoxycarbonyl-1,2-dihydroquinoline, in an inert solvent, for example a halogenated hydrocarbon such as dichloromethane, an ether such as tetrahydrofuran or dioxane, an amide such as DMF or dimethylacetamide, a nitrile such as acetonitrile, or in mixtures of these solvents, at temperatures between about –10 and 40, preferably between 0 and 30°.

In place of II, it is also possible to employ suitable reactive derivatives of these substances in the reaction, for example those in which reactive groups are temporarily blocked by protective groups. The amino acid derivatives II can be used, for example, in the form of their activated esters, which are preferably formed in situ, for example by adding HOBt or N-hydroxysuccinimide.

The starting materials of the formula II are, as a rule, novel. They can be prepared by known methods, for example the abovementioned methods of peptide synthesis and the elimination of protective groups.

As a rule, firstly protected peptide esters of the formula R'-M'-OR" are synthesized, where M' corresponds to the radical M reduced by one H atom at the N-terminal end, for example BOC-M'-OMe or Fmoc-M'-OMe. These are hydrolyzed to acids of the formula R'-M'-OH, for example BOC-M'-OH or Fmoc-M'-OH, and then condensed with a compound of the formula III, which is, where appropriate, likewise provided by appropriate protective groups at positions intended not to be available for the reactions.

In the case of compounds of the formula III, peptide esters of the formula R'-Q-Z'-R" are likewise synthesized, such as, for example, BOC-QZ'-OMe or Fmoc-Q-Z'-OMe where Z' is —NH— or —O—, and then the protective group R' is eliminated in a known manner, for example Fmoc by treatment with a piperidine/DMF solution, before the condensation is carried out to prepare compounds of the formula I.

It is possible and particularly advantageous to use the newer methods of peptide synthesis by modified Merrifield techniques and using peptide synthesizers as described, for example, in Peptides, Proc. 8th Am. Pept. Symp., Eds. V. Hruby and D. H. Rich, Pierce Comp. III, p. 73–77 (1983) by A. Jonczyk and J. Meinenhofer (Fmoc strategy) or the techniques described in Angew. Chem. 104, 375–391 (1992). Methods of these types are known per se, and description thereof here can therefore be dispensed with.

A base of the formula I can be converted with an acid into the relevant acid addition salt. Acids particularly suitable for this reaction are those which provide physiologically acceptable salts. Thus, it is possible to use inorganic acids, for example sulfuric acid, nitric acid, hydrohalic acids such as hydrochloric acid or hydrobromic acid, phosphoric acids such as orthophosphoric acid, sulfamic acid, also organic acids, especially aliphatic, alicyclic, araliphatic, aromatic or heterocyclic mono- or polybasic carboxylic, sulfonic or sulfuric acids, for example formic acid, acetic acid, propionic acid, pivalic acid, diethylacetic acid, malonic acid, succinic acid, pimelic acid, fumaric acid, maleic acid, lactic acid, tartaric acid, malic acid, benzoic acid, salicylic acid, 2- or 3-phenylpropionic acid, citric acid, gluconic acid, ascorbic acid, nicotinic acid, isonicotinic acid, methane- or ethanesulfonic acid, ethanedisulfonic acid, 2-hydroxyethanesulfonic acid, benzenesulfonic acid, p-toluenesulfonic acid, naphthalenemono- and -disulfonic acids, lauryl sulfuric acid. Salts with physiologically unacceptable acids, for example picrates, can be used for isolating and/or purifying the compounds of the formula I.

On the other hand, an acid of the formula I can be converted by reaction with a base into one of its physiologically acceptable metal or ammonium salts. Suitable salts in this case are, in particular, the sodium, potassium, magnesium, calcium and ammonium salts, also substituted ammonium salts, for example the dimethyl-, diethyl- or diisopropylammonium salts, monoethanol-, diethanol- or triethanolammonium salts, cyclohexyl, dicyclohexylammonium salts, dibenzylethylenediammonium salts, furthermore, for example, salts with N-methyl-D-glucamine or with arginine or lysine.

The invention furthermore relates to synthetic peptide layers consisting of one or more peptides of the formula I according to Claim 1, which are covalently bonded via a -sulfur- or -S-S- bridge to gold surfaces, characterized in that the C-terminal groups are linked in amide fashion to another peptide sequence with donor properties so that linkages to appropriate acceptor molecules can be produced.

The peptide derivatives of the formula I which are covalently bonded at the N terminus via sulfur-containing anchors to gold surfaces can be substituted at the C terminus by other peptides or lipids organize themselves on the gold surface to give single layers especially when self-organization is assisted by long hydrophobic radicals on the sulfur-containing anchors, or the conformation of the peptides favors layer formation. It is possible to measure the organization and density of these layers by physical methods such as cyclovoltametry and impedance spectrometry as long as there is a change in the capacity and/or the resistance due to long hydrophobic chains.

These single layers present peptide structures away from the gold layer which are able to act as ligands for acceptor molecules. An interaction between bound ligands and the acceptor molecules can be measured, for example, by surface plasmon resonance.

Peptide layers of these types can accordingly be used for investigating acceptor molecules of a wide variety of types. Examples of suitable acceptor molecules are receptors, enzymes, pump or channel proteins. Pump or channel proteins, and also receptors which extend through membranes, bind only if they are able simultaneously to incorporate into a lipid layer. These peptides can therefore act, either directly or coupled to a lipid, as ligands for acceptor molecules.

The model can therefore be used, for example, for a screening test for inhibitors, for ion pumps, to investigate ion channels or for construction for sensors of substrates and inhibitors of pump proteins. It is possible in this way for example to detect herbicides which inhibit the photochemical reaction center.

The single layers can be provided with a second layer by incubation with liposomes, in which case the hydrophobic and hydrophilic layers arrange themselves so that the central hydrophobic bilayer is bounded on the side of the gold surface by the hydrophilic peptide layer and away from the gold surface into the aqueous medium by a hydrophilic layer of the former liposome. The length of the peptide chain, especially in its 3-dimensional folding, thus determines the thickness of the hydrophilic layer next to the gold.

These bilayers simulate cell membranes and are capable of stable incorporation of, for example, transmembrane proteins (for example receptors). It is possible to insert channel-forming or ion-transporting proteins and to investigate their function, for example by impedance spectrometry.

The invention likewise relates to synthetic cell membranes, characterized in that they consist of a gold support which is covalently bonded to a peptide of the formula I according to Claim 1 via a sulfur bridge, with the C-terminal side of the peptide in turn being linked to lipid residues which in turn form, with liposomes which are present, a membrane-analogous lipid bilayer.

To construct the synthetic membranes, the monomolecular peptide layers which are covalently bonded via peptide spacers to a gold surface are provided with a second lipid layer, by rolling out liposomes or by the Langmuir-Blodgett technique, to result in defined lipid bilayers which represent a model of a biological membrane to the extent that they are adjacent to an aqueous phase on both sides. The peptide spacer in this case acts to form a hydrophilic layer between the hydrophobic lipid layer and the gold surface.

The C-terminal groups of the peptides are able to couple in amide fashion to lipids which have an $NH_2$ group, for example to dimyristoylphosphatidylamine, dipalmitoylphosphatidylamine, dioleylphosphatidylamine, natural cephalins, natural phosphatidylethanolamines and to long-chain primary amines, for example dodecylamine.

The coupling may take place in situ or ex situ, that is to say in solution. In the latter case, the complete molecule binds to the gold.

In all cases, the final result is a construct consisting of lipid which has long hydrophobic chains and which is bound via the peptide as spacer to the gold. It is alternatively possible to use Pt, Pd, Ag or Cu. These compounds have a tendency to self-organization.

They are capable of insertion of functional membrane proteins and thus permit, for example, their electrical, structural and binding properties to be investigated.

Liposomes consisting of phosphatidyicholine and phosphatidic acid are particularly suitable for forming the bilayers.

Defined bilayers are formed by fusion of liposomes above the transition temperature of the lipid. A formation of these bilayers has been measured in real time by surface plasmon resonance spectroscopy (SPRS). Liposomes with incorporated ATPase from chloroplasts ($CF_0F_1$) and from E. coli ($EF_0F_1$) form bilayers with inserted protein.

This has been demonstrated by SPRS: the layer thickness for the "empty" bilayer is 4.0 nm and for the bilayer with incorporated ATPase is 6.0 or 8.5 nm depending on the concentration of the ATPases. By comparison, the calculated layer thickness of an empty bilayer is 5 nm and the extended length of the ATPase is 8.5 nm. The packing density of the layers was determined by X-ray reflectrometry. It is 100% for the peptide layer and 60% for the monolayer. The composition of the monolayer covalently bonded to the gold was demonstrated by FTIR spectroscopy. The capacity was determined by cyclovoltammetry and impedance spectrometry (2 or 1 $\mu F/cm^2$). The activity of the enzyme in the lipid bilayer was demonstrated by coupling the proton translocation to the discharge of the protons on the gold electrode with rapid pulse techniques such as double-potential-step chromoamperometry and square wave voltammetry. The latter technique can be used for quantitative determination of the enzyme activity, it being necessary to take account of the effect of the electric field. In addition, the activity can be measured as a function of the activation potential. In all the measurements, the bilayer is retained with the incorporated enzyme even after rinsing with buffer. The measurements can be carried out several times on the same sample. The activity can be suppressed by known specific inhibitors.

The immobilization of enzymes on the gold surface opens up possibilities for determining the structure and conformation of the membrane proteins by atomic force microscopy and other methods of surface physics.

Apart from the pump protein, it is likewise possible in general to insert ion channel-forming proteins, ionophores and enzymes.

It is furthermore possible to incorporate various types of receptors in the membrane. It is then also possible, for example, with the aid of measurements of layer thickness, for example by surface plasmon resonance spectroscopy, to investigate not only static effects but also dynamic processes on the receptor.

The invention accordingly furthermore relates to synthetic cell membranes, characterized in that the bilayer is limited on the side of the gold surface by the hydrophilic peptide layer and in the direction of the other side which projects into the aqueous medium by the hydrophilic head groups of the former liposomes, with proteins being stably incorporated in the membranes.

The invention likewise relates to synthetic cell membranes which contain light-driven proteins such as, for example, bacteriorhodopsin and thus can be used as solar cells. A solar cell of this type can be constructed, for example, by applying a peptide layer, lipid monolayer or lipid bilayer, and a layer of the photo-sensitive pump protein, in the stated sequence, to a metal electrode, preferably a noble metal electrode consisting of Au, Pt, Pd or Cu. A layer structure of this type is suitable for transferring the self-potential of the pump protein, which it assumes on illumination, to the electrode, and forming a blocking layer for the protons, which are then transported by the protein so that their back-diffusion is impeded. The protons are discharged on the metal electrode. This makes use of the potential set up on the electrode by the illumination. This potential can be modulated by suitable interruption of the illumination so that the potential set up on the electrode is one with which hydrogen evolution occurs. This results in spontaneous, that is to say without applying a voltage, hydrogen evolution. It is thus possible to generate hydrogen by illuminating the modified cell membrane.

Alternatively, current can be generated directly if hydrogen formed at the cathode is reduced back to protons at the anode.

The invention furthermore relates to a process for producing the synthetic cell membranes, characterized in that a gold-coated substrate is introduced into a solution of a peptide or a peptide-analogous compound of the formula I which is, for example, activated by treatment with diisopropylcarbodiimide, coupled to the lipid component and converted into a defined lipid bilayer by adding liposomes. The liposomes may comprise proteins of various types, with those already mentioned being particularly suitable.

The membranes are produced by adsorbing the peptides of the formula I, which have disulfide or S-H groups or free carboxyl groups, for example on a glass support which has undergone gold vapor deposition, so that the peptide is connected covalently via an Au-S-C linkage to the gold support. These peptide constructs are coupled in situ via activation of the COOH group with, for example, diisopropylcarbodiimide, for example with dimyristoylphosphatidylethanolamine, so that a lipid monolayer is produced on the gold substrate and is linked to the gold via the peptide spacer molecule. The monolayer is formed by self-organization (self assembly) on coupling, because the long myristoyl radicals tend to aggregate parallel to the chain. Such monolayers form in the presence of liposomes, without and with incorporated transmembrane proteins, defined bilayers which are stably attached to the support.

However, it is particularly advantageous to synthesize a molecule which consists from the outset of a hydrophilic spacer and a lipid or long-chain alkyl compound which bonds covalently to gold via a terminal SH or -S-S- group and which arranges itself by self-organization (self assembly).

The coupling need therefore not necessarily take place in situ.

Furthermore, the invention relates to the use of the synthetic cell membranes for investigating (a) interactions of ligand and acceptor molecules in membrane models;

(b) receptor binding processes and for carrying out receptor binding assays;

(c) processes which take place in ion channels with ion channel-forming proteins and (d) the activity of pharmaceuticals, for example with regard to their association with membranes and/or their toxic effect.

The invention furthermore relates to the use of the synthetic cell membranes for constructing sensors, especially biosensors, and for constructing bioelectronic components.

All temperatures are stated hereinbefore and hereinafter in °C. In the following examples, "usual workup" means: if necessary, water is added, neutralization, extraction with ether or dichloromethane and separation are carried out, the organic phase is dried over sodium sulfate, filtered and evaporated, and purification is carried out by chromatography on silica gel and/or HPLC. RT=retention time (minutes) in HPLC on Lisorb® select B (250×4 column, mobile phase: 0.3% TFA in water; 0–80% by volume isopropanol gradient in 50 min at a flow rate of 1 ml/min and detection at 215 nm. $M^++1$=molecular peak in the mass spectrum obtained by the fast atom bombardment method (FAB), usually stands for $M^++H$, that is to say the mass of a particular compound increased by 1 mass unit.

The substances were, as a rule, synthesized by prior art methods on a Wang resin using a Fmoc strategy with acid-labile side protective groups. The N-terminal derivatization was achieved by reaction with C-tritylmercaptopropionic acid or lipoic acid. After elimination with trifluoroacetic acid/dichloromethane/anisole and ether precipitation, the crude product was, in the case of the trityl derivatives, subjected to gel filtration on Sephadex G10®, dissolving in triphenylmethanol/trifluoroacetic acid/water, and purified by HPLC. No triphenylmethanol was used in the case of lipoic acid.

The following examples are intended to describe the invention in detail without, however, restricting it.

It is assumed that a skilled person will be able, even without further statements, to utilize the above description in the widest scope. The preferred embodiments are therefore to be interpreted only as descriptive, and by no means in any way limiting, disclosure.

The complete disclosure of all applications, patents and publications mentioned hereinbefore and hereinafter, and of the corresponding application P 44 44 893.7, filed on Dec. 16, 1994, are incorporated into this application by reference.

EXAMPLES

Example 1

0.6 g of Fmoc-Lys(BOC)-OH is dissolved in 100 ml of dichloromethane and, after addition of 1.2 equivalents of Wang resin (p-benzyloxybenzyl alcohol-resin), 1.2 equivalents of HOBt and 1.2 equivalents of DIC, stirred at room temperature for 12 hours. Removal of the solvent results in Fmoc-Lys(BOC)-Wang resin. Condensation in a peptide synthesizer of Fmoc-Pro-OH with H-Lys(BOC)-Wang resin [liberated from Fmoc-Pro-Wang resin with piperidine/DMF (20%)] is carried out by employing a three-fold excess of the protected proline. The coupling is carried out in DCCI/HOBt at room temperature. Fmoc-Pro-Lys(BOC)-Wang resin is obtained. Subsequent renewed treatment with piperidine/DMF (20%) affords H-Pro-Lys(BOC)-Wang resin.

Example 2

In analogy to Example 1, Fmoc-Ala-Ala-Ala-Ala-Ala-OH (SEQ ID NO:11) is obtained starting from Fmoc-Ala-Wang resin by multiple condensation with Fmoc-Ala-OH in a peptide synthesizer (continuous flow principle) after carrying out the following steps:

- liberation of H-Ala-Wang resin with piperidine/DMF (20%)
- reaction with Fmoc-Ala-OH in DCCI/HOBt at room temperature
- washing and treatment with piperidine/DMF (20%)
- coupling of the resulting H-Ala-Ala-Wang resin with Fmoc-Ala-OH
- washing and treatment of the resulting Fmoc-Ala-Ala-Ala-Wang resin with piperidine/DMF and subsequent repetition of the condensation step twice with Fmoc-Ala-OH.

Liberation of H-Ala-Ala-Ala-Ala-Ala-Wang resin (SEQ ID NO:12) takes place by treatment with piperidine/DMF (20%)

Fmoc-Gly-Gly-Gly-OH is obtained analogously.

Example 3

In analogy to Example 2, Fmoc-Ala-Ser(But)-Ser(But)-Ala-Ala-Ser(But)-Ala-OH (SEQ ID NO:13) is obtained starting from Fmoc-Ala-Wang resin after carrying out the appropriate reaction steps and reintroduction of the side-chain protective groups (butylation of Ser) by coupling with Fmoc-Ser(But)-OH, Fmoc-Ala-OH, Fmoc-Ala-OH, Fmoc-Ser(But)-OH, Fmoc-Ser(But)-OH and Fmoc-Ala-OH in the stated sequence.

Subsequent treatment with piperidine/DMF (20%) affords:

H-Ala-Ser(But)-Ser(But)-Ala-Ala-Ser(But)-Ala-OH (SEQ ID NO:14).

Example 4

In analogy to Example 2, Fmoc-Gly-Gly-Gly-Arg(Mtr)-Gly-Asp(OBut)-Ser(But)-Pro-Lys(BOC)-Wang resin (SEQ ID NO:15) is obtained starting from H-Pro-Lys(BOC)-Wang resin after carrying out the appropriate reaction steps and reintroduction of the side-chain protective groups by coupling with Fmoc-Ser(But)-OH, Fmoc-Asp(OBut)-OH, Fmoc-Gly-OH, Fmoc-Arg(Mtr)-OH and Fmoc-Gly-Gly-Gly-OH in the stated sequence.

Subsequent treatment with piperidine/DMF (20%) affords:

H-Gly-Gly-Gly-Arg(Mtr)-Gly-Asp(OBut)-Ser(But)-Pro-Lys(BOC)-Wang resin (SEQ ID NO:16).

Example 5

0.4 g of H-Gly-Gly-Gly-Arg(Mtr)-Gly-Asp(OBut)-Ser(But)-Pro-Lys(BOC)-Wang resin (SEQ ID NO:16) is condensed in a peptide synthesizer (continuous flow principle) with Trt-S—$(CH_2)_2$—CO—NH—$(CH_2)_{10}$—COOH (RT 35.9 min, M$^+$+1=531) by employing a three-fold excess of the acid. The coupling is carried out in DCCI/HOBt at room temperature. Trt-S—$(CH_2)_2$—CO—NH—$(CH_2)_{10}$, -CO-Gly-Gly-Gly-Arg(Mtr)-Gly-Asp(OBut)-Ser(But)-Pro-Lys(BOC)-Wang resin (SEQ ID NO:17) is obtained. Subsequent treatment with TFA/$CH_2Cl_2$ in the presence of water affords Trt-S—$(CH_2)_2$, —CO—NH—$(CH_2)_{10}$, -CO-Gly-Gly-Gly-Arg(Mtr)-Gly-Asp(OBut)-Ser(But)-Pro-Lys(BOC)-OH (SEQ ID NO:18).

Analogous condensation of Trt-S—$(CH_2)_2$—CO—NH—$(CH_2)_{10}$—COOH
with H-Ala-Ala-Ala-Ala-Ala-Wang resin (SEQ ID NO:12) and subsequent elimination from the resin results in:
Trt-S—$(CH_2)_2$—CO—NH—$(CH_2)_{10}$—CO-Ala-Ala-Ala-Ala-Ala-OH (SEQ ID NO:19);
with H-Ala-Ser(But)-Ser(But)-Ala-Ala-Ser(But)-Ala-Wang resin (SEQ ID NO:20) and subsequent elimination from the resin results in:
Trt-S—$(CH_2)_2$—CO—NH—$(CH_2)_{10}$—CO-Ala-Ser-Ser-Ala-Ala-Ser-Ala-OH (SEQ ID NO:21).

Example 6

In analogy to Example 5, condensation of H-Gly-Gly-Gly-Arg(Mtr)-Gly-Asp(OBut)-Ser(But)-Pro-Lys(BOC)-Wang resin (SEQ ID NO:16) in a peptide synthesizer (continuous flow principle) with HS—$(CH_2)_2$—CO—NH—$(CH_2)_{10}$—COOH result in HS—$(CH_2)_2$—CO—NH—$(CH_2)_{10}$—CO-Gly-Gly-Gly-Arg(Mtr)-Gly-Asp(OBut)-Ser(But)-Pro-Lys(BOC)-Wang resin (SEQ ID NO:43). Subsequent treatment with TFA/$CH_2Cl_2$ in the presence of water affords HS—$(CH_2)_2$—CO—NH—$(CH_2)_{10}$—CO-Gly-Gly-Gly-Arg-Gly-Asp-Ser-Pro-Lys-OH (SEQ ID NO:44).

Analogous condensation of HS—$(CH_2)_2$—CO—NH—$(CH_2)_{10}$—COOH
with H-Ala-Ala-Ala-Ala-Ala-Wang resin (SEQ ID NO:12) and subsequent elimination from the resin results in:
HS—$(CH_2)_2$—CO—NH—$(CH_2)_{10}$—CO-Ala-Ala-Ala-Ala-Ala-OH (SEQ ID NO:22);
with H-Ala-Ser(But)-Ser(But)-Ala-Ala-Ser(But)-Ala-Wang (SEQ ID NO:20) resin and subsequent elimination from the resin results in:
HS—$(CH_2)_2$—CO—NH—$(CH_2)_{10}$—CO-Ala-Ser-Ser-Ala-Ala-Ser-Ala-OH (SEQ ID NO:23).

Example 7

In analogy to Example 5, condensation of H-Gly-Gly-Gly-Arg(Mtr)-Gly-Asp(OBut)-Ser(But)-Pro-Lys(BOC)-Wang resin (SEQ ID NO:16) in a peptide synthesizer (continuous flow principle) with Trt-S—$(CH_2)_2$—COOH (RT 34.5 min, $M^++1=347$) results in Trt-S—$(CH_2)_2$—CO-Gly-Gly-Gly-Arg(Mtr)-Gly-Asp (OBut)-Ser(But)-Pro-Lys (BOC)-Wang resin (SEQ ID NO:24). Subsequent treatment with TFA/$CH_2Cl_2$ in the presence of water affords Trt-S—$(CH_2)_2$—CO-Gly-Gly-Gly-Arg-Gly-Asp-Ser-Pro-Lys-OH (SEQ ID NO:25).

Analogous condensation of Trt-S—$(CH_2)_2$—COOH with H-Ala-Ala-Ala-Ala-Ala-Wang resin (SEQ ID NO:12) and subsequent elimination from the resin results in Trt-S—$(CH_2)_2$—CO-Ala-Ala-Ala-Ala-Ala-OH (SEQ ID NO:6); with H-Ala-Ser-Ser-Ala-Ala-Ser-Ala-Wang resin (SEQ ID NO:20) and subsequent elimination from the resin results in Trt-S—$(CH_2)_2$—CO-Ala-Ser-Ser-Ala-Ala-Ser-Ala-OH (SEQ ID NO:4).

Example 8

In analogy to Example 5, condensation of H-Gly-Gly-Gly-Arg(Mtr)-Gly-Asp(OBut)-Ser(But)-Pro-Lys(BOC)-Wang resin (SEQ ID NO:16) in a peptide synthesizer (continuous flow principle) with 1,2-dithiolane-3-pentanoic acid (lipoic acid) results in lipoyl-Gly-Gly-Gly-Arg(Mtr)-Gly-Asp(OBut)-Ser(But)-Pro-Lys(BOC)-Wang resin (SEQ ID NO:45). Subsequent treatment with TFA/$CH_2Cl_2$ in the presence of water affords lipoyl-Gly-Gly-Gly-Arg-Gly-Asp-Ser-Pro-Lys-OH (SEQ ID NO:46).

Analogous condensation of lipoic acid with H-Ala-Ala-Ala-Ala-Ala-Wang resin (SEQ ID NO:12) and subsequent elimination from the resin results in lipoyl-Ala-Ala-Ala-Ala-Ala-OH (SEQ ID NO:47); RT 21.7 min, $M^++1=562$; with H-Ala-Ser(But)-Ser(But)-Ala-Ala-Ser(But)-Ala-Wang resin and subsequent elimination from the resin results in lipoyl-Ala-Ser-Ser-Ala-Ala-Ser-Ala-OH (SEQ ID NO:48).

Example 9

0.3 g of Trt-S—$(CH_2)_2$—CO—NH—$(CH_2)_{10}$—CO-Gly-Gly-Gly-Arg(Mtr)-Gly-Asp(OBut)-Ser(But)-Pro-Lys (BOC)-OH (SEQ ID NO:18) is taken up in 30 ml of 2 N HCl based on dioxane and stirred at room temperature for 2 hours. The reaction mixture is subsequently evaporated to dryness, and the residue is treated with TFA/$CH_2Cl_2$/anisole, precipitated by adding diethyl ether, dissolved in triphenylmethanol/TFA/water and subjected to gel filtration on Sephadex G10®. Subsequent purification by HPLC affords Trt-S—$(CH_2)_2$—CO—NH—$(CH_2)_{10}$—CO-Gly-Gly-Gly-Arg-Gly-Asp-Ser-Pro-Lys-OH (SEQ ID NO:9).

Obtained analogously by removing the protective groups starting
from Trt-S—$(CH_2)_2$—CO—NH—$(CH_2)_{10}$—CO-Ala-Ser(But)-Ser(But)-Ala-Ala-Ser(But)-Ala-OH is (SEQ ID NO:29):
Trt-S—$(CH_2)_2$—CO—NH—$(CH_2)_{10}$—CO-Ala-Ser-Ser-Ala-Ala-Ser-Ala-OH (SEQ ID NO:21);
from Trt-S—$(CH_2)_2$—CO-Gly-Gly-Gly-Arg(Mtr)-Gly-Asp(OBut)-Ser(But)-Pro-Lys(BOC)-OH (SEQ ID NO:30) is:
Trt-S—$(CH_2)_2$—CO-Gly-Gly-Gly-Arg-Gly-Asp-Ser-Pro-Lys-OH (SEQ ID NO:25);
from Trt-S—$(CH_2)_2$—CO-Ala-Ser(But)-Ser(But)-Ala-Ala-Ser(But)-Ala-OH (SEQ ID NO:30) is:
Trt-S—$(CH_2)_2$—CO-Ala-Ser-Ser-Ala-Ala-Ser-Ala-OH (SEQ ID NO:4); RT 33.0 min, $M^++1=895$.

Example 10

In analogy to Example 5, condensation of H-Gly-Gly-Gly-Arg(Mtr)-Gly-Asp(OBut)-Ser(But)-Pro-Lys(BOC)-Wang resin (SEQ ID NO:16) in a peptide synthesizer (continuous flow principle) with HS—$(CH_2)_2$—COOH results in HS—$(CH_2)_2$—CO-Gly-Gly-Gly-Arg(Mtr)-Gly-Asp(OBut)-Ser(But)-Pro-Lys(BOC)-Wang resin (SEQ ID NO:32). Subsequent treatment with TFA/$CH_2Cl_2$ in the presence of water affords HS—$(CH_2)_2$—CO-Gly-Gly-Gly-Arg-Gly-Asp-Ser-Pro-Lys-OH (SEQ ID NO:49).

Analogous condensation of HS—$(CH_2)_2$—COOH with H-Ala-Ala-Ala-Ala-Ala-Wang resin (SEQ ID NO:12) and subsequent elimination from the resin results in HS—$(CH_2)_2$—CO-Ala-Ala-Ala-Ala-Ala-OH (SEQ ID NO:22); with H-Ala-Ser(But)-Ser(But)-Ala-Ala-Ser(But)-Ala-Wang resin (SEQ ID NO:20) and subsequent elimination from the resin results in HS—$(CH_2)_2$—CO-Ala-Ser-Ser-Ala-Ala-Ser-Ala-OH (SEQ ID NO:5).

Example 11

0.5 g of HS—$(CH_2)_2$—CO—NH—$(CH_2)_{10}$—CO-Gly-Gly-Gly-Arg(Mtr)-Gly-Asp(OBut)-Ser(But)-Pro-Lys (BOC)-OH (SEQ ID NO:33) is taken up in 30 ml of 2 N HCl based on dioxane and stirred at room temperature for 2 hours. The reaction mixture is subsequently evaporated to dryness, and the residue is treated with TFA/$CH_2Cl_2$/anisole, precipitated by adding diethyl ether, dissolved in TFA/water and subjected to gel filtration on Sephadex G10®. Subsequent purification of HPLC affords HS—$(CH_2)_2$—CO—NH—$(CH_2)_{10}$—CO-Gly-Gly-Gly-Arg-Gly-Asp-Ser-Pro-Lys-OH (SEQ ID NO:10).

Obtained analogously by removing the protective groups starting
from HS—$(CH_2)_2$—CO—NH—$(CH_2)_{10}$—CO-Ala-Ser(But)-Ser(But)-Ala-Ala-Ser(But)-Ala-OH (SEQ ID NO:34) is:
HS—$(CH_2)_2$—CO—NH—$(CH_2)_{10}$—CO-Ala-Ser-Ser-Ala-Ala-Ser-Ala-OH (SEQ ID NO:23);
from HS—$(CH_2)_2$—CO-Gly-Gly-Gly-Arg(Mtr)-Gly-Asp(OBut)-Ser(But)-Pro-Lys(BOC)-OH (SEQ ID NO:50) is:
HS—$(CH_2)_2$—CO-Gly-Gly-Gly-Arg-Gly-Asp-Ser-Pro-Lys-OH (SEQ ID NO:49);
from HS—$(CH_2)_2$—CO-Ala-Ser(But)-Ser(But)-Ala-Ala-Ser(But)-Ala-OH (SEQ ID NO:35) is:
HS—$(CH_2)_2$—CO-Ala-Ser-Ser-Ala-Ala-Ser-Ala-OH (SEQ ID NO:5); RT 2.9 min, $M^++1=652$;
from lipoyl-Gly-Gly-Gly-Arg(Mtr)-Gly-Asp(OBut)-Ser(But)-Pro-Lys(BOC)-OH (SEQ ID NO:45) is:
lipoyl-Gly-Gly-Gly-Argy-Gly-Asp-Ser-Pro-Lys-OH (SEQ ID NO:46);
from lipoyl-Ala-Ser(But)-Ser(But)-Ala-Ala-Ser(But)-Ala-OH (SEQ ID NO:51) is:
lipoyl-Ala-Ser-Ser-Ala-Ala-Ser-Ala-OH (SEQ ID NO:48).

The following examples relate to peptide monolayers and lipid bilayers.

Example A

Gold electrodes composed of gold applied by electrothermal vapor deposition on glass with an area of 0.9 $cm^2$ are cleaned in chromic acid overnight, then rinsed with water and subsequently with methanol, and dried. The electrodes cleaned in this way are placed in a solution of a mercapto- or tritylmercaptopeptide of the formula I in trifluoroacetic acid (1 mg/ml) and incubated therein for 96 hours. They are then rinsed successively with dimethylformamide (DMF) and dichloromethane and dried.

The following peptide layers bound to gold are obtained:

(a) $Au_x$-[S—$(CH_2)_2$—CO-Ala-Ser-Ser-Ala-Ala-Ser-Ala-OH]$_y$ (SEQ ID NO:39);
(b) $Au_x$-[S—$(CH_2)_2$—CO-Ala-Ser-Ser-Ala-Ala-Ser-Ala-OH]$_y$ (SEQ ID NO:39);
(c) $Au_x$-[S—$(CH_2)_2$—CO-Ala-Ala-Ala-Ala-Ala-OH]$_y$ (SEQ ID NO:40);
(d) $Au_x$-[S—$(CH_2)_2$—CO-Ala-Ala-Ala-Ala-Ala-OH]$_y$ (SEQ ID NO:40);
(e) $Au_x$-[5-(1,2-dithio-3-cyclopentanyl)pentanoyl-Ala-Ala-Ala-Ala-Ala-OH]$_y$ (SEQ ID NO:41);
(f) $Au_x$-[S—$(CH_2)_2$—CO—NH—$(CH_2)_{10}$—CO-Gly-Gly-Gly-Arg-Gly-Asp-Ser-Pro-Lys-OH]$_y$ (SEQ ID NO:42);
(g) $Au_x$-[S—$(CH_2)_2$—CO—NH—$(CH_2)_{10}$—CO-Gly-Gly-Gly-Arg-Gly-Asp-Ser-Pro-Lys-OH]$_y$ (SEQ ID NO:42).

The indices "x" and "y" are intended to indicate that these are polymolecular units.

Example B

Coupling of the peptide layers with dimyristoylphosphatidylethanolamine (DMPE) to produce the lipid monolayers (in situ coupling)

Gold electrodes (a) to (g) coated with the peptides as described above are activated in a [sic] solution of DMPE (1 mg/ml), HOBT (0.2 mg/ml) and LiCl (5 mg/ml) in a mixture of DMF and dichloromethane (1:1) with diisopropyicarbodiimide (40 µl/ml). After addition of N-ethyldiisopropylamine they are subsequently incubated for 96 hours. This coupling procedure is carried out once more with fresh solutions, whereupon the monolayer forms. Finally, the electrodes are rinsed with DMF and dichloromethane and dried.

Example C

Production of Lipid Bilayers

The electrodes coated with a lipid monolayer are incubated in a liposome suspension with and without the incorporated ATPase from *E.coli*: $EF_0F_1$ (Lipid* 0.24 mg/ml, $EF_0F_1$ 18 nmol/l) at 30° C. for 30 min. Phosphatidylcholine is used as lipid.

Alternatively, they are provided with the second lipid layer, for example of phosphatidylcholine and phosphatidic acids, by means of the Langmuir-Schäfer or the Langmuir-Blodgett technique (Lit. loc. cit.). The enzyme is likewise inserted into the "empty" bilayers in contact with liposomes with incorporated ATPase.

Tests with the Bilayers

The formation of the bilayers is followed by surface plasmon resonance spectroscopy. The layer thickness of the bilayer with and without the enzyme was determined to be 8.5 and 4 nm. The former corresponds to the extended length of the ATPase, whereas the "empty" bilayer ought to have a layer thickness of 4–5 nm. This demonstrates the incorporation of the enzyme in the bilayer.

The density of the layers is checked by cyclic voltametry and impedance spectrometry.

ATPase $EF_0F_1$ is an enzyme which catalyzes the hydrolysis of ATP and, coupled therewith, the translocation of protons through the membrane. It is therefore possible to demonstrate functioning of the enzyme via the change in the proton concentration at the gold electrode. The proton concentration is measured by square wave voltammetry of the discharge of protons to give hydrogen. It emerges that the signal of the discharge of protons increases with the ATP concentration in the solution.

Example D

Lipid bilayers in which the ATPase $CF_0F_1$ from chloroplasts is incorporated are produced in analogy to Example C.

Example E

Lipid bilayers in which the bacteriorhodopsin from halobacteria is incorporated are produced in analogy to Example C.

We claim:

1. A peptide or modified peptide of formula I

R-A-B-C-D-E-OH     I, in which

A is an amino acid residue selected from a group consisting of Ala, Gly and Leu, B is an amino acid or dipeptide residue selected from a group consisting of Ala, Ser, Gly-Gly and Ser-Ser, C is a residue selected from a group consisting of Ala, Ala-Ala, Leu-Leu, Ala-Ala-Ala, Arg-Gly-Asp and Leu-Leu-Leu, D is an amino acid residue selected from a group consisting of Ala and Ser, E is an amino acid or dipeptide residue selected from a group consisting of Ala, Leu and Pro-Lys, R is HS-alkyl-CO, HS-alkyl-CO-NH-alkyl'-CO-, Trt-S-alkyl-CO-, Trt-S-alkyl-CO-NH-alkyl'-CO- or 1,2-dithiocyclopentane-3-$(CH_2)_4$—CO-, alkyl and alkyl' are each, independently of one another, an alkylene radical with 1 to 11 C atoms and Trt is triphenylmethyl, and the salts thereof.

2. A process for the preparation of a compound of formula I of claim 1, comprising liberating said compound from a functional derivative thereof by treating with a solvolyzing or hydrogenolyzing agent, or reacting a compound of formula II

M-OH     II wherein

M is R, R-A, R-A-B, R-A-Gly, R-A-B-C, R-A-B-Leu, R-A-B-Arg, R-A-B-Arg-Gly or R-A-B-C-D with an amino compound of formula III

H-Q-OH     III wherein

Q is E, Lys, D-E, C-D-E, Leu-D-E, Asp-D-E, Gly-Asp-D-E, B-C-D-E, Gly-C-D-E, A-B-C-D-E or NH-alkyl'-CO-A-B-C-D-E.

3. A synthetic peptide layer comprising one or more peptides of formula I according to claim 1, wherein said peptide(s) are covalently bonded via sulfur bridges to a gold surface, and wherein the C-terminal groups of said peptides are linked by an amide bond to another peptide sequence with donor properties so that linkages to appropriate acceptor molecules can be produced.

4. A synthetic cell membrane, which comprises a gold, Pt, Pd, Ag or Cu support which is covalently bonded to a peptide of formula I according to claim 1 via a sulfur bridge, wherein the C-terminal end of the peptide in turn is linked to lipid residues which in turn form, with liposomes which are present, a membrane-analogous lipid bilayer.

5. The synthetic cell membrane according to claim 4, wherein said lipid bilayer, which comprises a hydrophilic peptide layer, is bound on one side by a gold surface and a hydrophilic peptide layers, and on the other side by said liposomes, which project via their hydrophilic layers into an aqueous medium, and wherein one or more proteins are stably incorporated in the membrane.

6. The synthetic cell membrane according to claim 4, which further comprises one or more inserted light-driven proteins and which can act as solar cell.

7. A process for the production of the synthetic cell membrane according to claim 5, comprising (a) introducing a substrate coated with Au, Pt, Pd, Ag or Cu into a solution of a peptide or modified peptide of formula I according to claim 1, thereby connecting the peptide to the metal, activating the peptide, coupling the peptide to said lipid residues, and adding liposomes, with or without incorporated protein, thereby forming a defined lipid bilayer, or (b) constructing the membranes by the Langmiur-Blodgett technique.

8. The process for the production of synthetic membranes according to claim 7, wherein said liposomes comprise transmembrane proteins.

9. A method for investigating the kinetics of ligand and acceptor molecule interactions, comprising contacting a ligand of interest with a synthetic cell membrane according to claim 4, wherein said membrane further comprises an acceptor of interest, and measuring the kinetics with which the ligand interacts with the acceptor.

10. A method for investigating processes which take place in ion channels, comprising introducing reactants of interest into the ion channels of a synthetic cell membrane according to claim 4, wherein said membrane comprises one or more ion channel-forming proteins, and measuring the results of the reaction.

11. A method for investigating the kinetics with which a test substance and an inserted membrane protein interact, comprising contacting a test substance of interest with a synthetic cell membrane according to claim 4, wherein said membrane further comprises an inserted protein of interest, and measuring the kinetics with which the ligand and the inserted protein interact.

12. A method of measuring the kinetics of receptor binding, comprising binding a ligand of interest to a synthetic cell membrane according to claim 4, wherein said membrane further comprises a receptor of interest, and assaying the binding of the ligand and the receptor as a function of time.

13. A method of investigating receptor binding processes, comprising contacting a substance of interest with a synthetic cell membrane according to claim 4, wherein said membrane comprises a receptor of interest, and measuring changes in said substance or said receptor.

14. In a sensor comprising a synthetic cell membrane, the improvement wherein said synthetic cell membrane is a synthetic cell membrane of claim 4.

15. The sensor of claim 14, wherein said sensor is a biosensor.

16. A method of investigating the activity of a pharmaceutical or a crop protection agent, comprising incubating said pharmaceutical or crop protection agent with a synthetic cell membrane according to claim 4, and measuring changes in said membrane.

* * * * *